(12) United States Patent
O'Connell et al.

(10) Patent No.: US 7,220,540 B1
(45) Date of Patent: May 22, 2007

(54) METHODS FOR DETECTING BACTERIOPHAGE MS2

(75) Inventors: Kevin P. O'Connell, Abingdon, MD (US); Akbar S. Khan, Joppa, MD (US); Cheng J. Cao, Glen Army, MD (US); Jennifer R. Bucher, Joppa, MD (US); Mark V. Gostomski, Bel Air, MD (US); James J. Valdes, Churchville, MD (US); Patricia E. Anderson, Baltimore, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 423 days.

(21) Appl. No.: 11/001,614

(22) Filed: Nov. 29, 2004

Related U.S. Application Data

(62) Division of application No. 10/328,226, filed on Dec. 23, 2002, now Pat. No. 6,841,346.

(60) Provisional application No. 60/383,999, filed on May 29, 2002.

(51) Int. Cl.
*C12Q 1/70* (2006.01)

(52) U.S. Cl. .................. 435/5; 435/4; 435/7.1
(58) Field of Classification Search .......... None
See application file for complete search history.

(56) References Cited

OTHER PUBLICATIONS

O'Connell Kevin P; Bucher Jennifer R; Anderson Patricia E; Cao Cheng J; Khan Akbar S; Gostomski Mark V; Valdes James J Real-time fluorogenic reverse transcription-PCR assays for detection of bacteriophage MS2. Applied and environmental microbiology. Jan. 2006, 72 (1) p. 478-83.*

Dreier, J., M. Störmer, and K. Kleesiek. 2005. Use of bacteriophage MS2 as an internal control in viral reverse transcription-PCR assays. J. Clin. Microbiol. 43:4551-4557.*

Rowe C A; Tender L M; Feldstein M J; Golden J P; Scruggs S B; MacCraith B D ; Cras J J; Ligler F S. Array biosensor for simultaneous identification of bacterial, viral, and protein analytes. Analytical chemistry. Sep. 1, 1999, 71 (17) p. 3846-52.*

* cited by examiner

*Primary Examiner*—Bruce R. Campell
*Assistant Examiner*—Stuart W. Snyder
(74) *Attorney, Agent, or Firm*—Ulysses John Biffoni

(57) ABSTRACT

The present invention relates to methods and assays for detecting bacteriophage MS2 in a sample.

1 Claim, 3 Drawing Sheets

```
attgcgctcg tgaaggcgta cactgccgct cgtcgcggta attggcgcca ggcgctccgc    60
tacctgcCC taaacgaaga tcgaaagttt cgatcaaaac acgtgccgg caggtggttg    120
gagttgcagt tcggttggtt accactaatg agtgatatcc aggtgcata tgagatgctt    180
acgaaggttc accttcaaga gtttcttcct atgagagccg tacgtcaggt cggtactaac    240
atcaagttag atggccgtct gtcgtatcca gctgcaaact tccagacaac gtgcaacata    300
tcgcgacgta tcgtgatatg gttttacata aacgatgcac gtttggcatg gttgtcgtct    360
ctaggtatct tgaacccact aggtatagtg tgggaaaagg tgcctttctc attcgttgtc    420
gactggctcc tacctgtagg gaggccttta gaggcctta cggccccgt gggatgctcc    480
tacatgtcag gaacagttac tgacgtaata acgggtgagt ccatcataag cgttgacgct    540
ccctacgggt ggactgtgga gagacaggc actgctaagg cccaaatctc agccatgcat    600
```

FIGURE 1A

```
cgaggggtac aatccgtatg gccaacaact ggcgcgtacg taaagtctcc tttctcgatg    660
gtccatacct tagatgcgtt agcattaatc aggcaacggc tctctagata gagccctcaa    720
ccggagtttg aagcatggct tctaacttta ctcagttcgt tctcgtcgac aatggcggaa    780
ctggcgacgt gactgtcgcc ccaagcaact tcgctaacgg ggtcgctgaa tggatcagct    840
ctaactcgcg ttcacaggct tacaaagtaa cctgtagcgt tcgtcagagc tctgcgcaga    900
atcgcaaata caccatcaaa gtcgaggtgc ctaaagtggc aacccagact gttggtggtg    960
tagagcttcc tgtagccgca tggcgttcgt acttaaatat ggaactaaac attccaattt   1020
tcgctacgaa ttccgactgc gagcttattg ttaaggcaat gcaaggtctc ctaaaagatg   1080
gaaacccgat tccctcagca atcgcagcaa actccggcat ctactaatag acgccggcca   1140
ttcaaacatg aggattaccc atgtcgaaga caacaaagaa gttcaactct ttatgtattg   1200
```

FIGURE 1B

```
atcttcctcg cgatctttct ctcgaaattt accaatcaat tgcttctgtc gctactgaa  1260
gcggtgatcc gcacagtgac gactttacag caattgctta cttaagggac gaattgctca  1320
caaagcatcc gaccttaggt tctggtaatg acgaggcgac ccgtcgtacc ttagctatcg  1380
ctaagctacg ggaggcgaat ggtgatcgcg gtcagataaa tagagaaggt ttcttacatg  1440
acaaatcctt gtcatgggat ccggatgttt tacaaaccag catccgtagc cttattggca  1500
acctcctctc tggctaccga tcgtcgttgt ttgggcaatg cacgttctcc aacggtgctc  1560
ctatggggca caagttgcag gatgcagcgc cttacaagaa gttcgctgaa caagcaaccg  1620
ttaccccccg cgctctgaga gcggctctat tggtccgaga ccaatgtgcg ccgtggatca  1680
gacacgcggt ccgctataac gagtcatatg aatttaggct cgttgtaggg aacggagtgt  1740
```

FIGURE 1C

SEQUENCE LISTING

<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: Probe 1

<400> SEQUENCE: 1
taaggcccaa atctcagcca tgcatc                                        26

<210> SEQ ID NO 2
<211> LENGTH: 31
<212> TYPE: DNA
<213> ORGANISM: Artificial Sequence
<220> FEATURE:
<223> OTHER INFORMATION: Probe 2

<400> SEQUENCE: 2
agaatcgcaa ataccaccatc aaagtcgagg t                                 31

<210> SEQ ID NO 3
<211> LENGTH: 30
<212> TYPE: DNA
<213> ORGANISM: Artificial Sequence
<220> FEATURE:

-continued

<223> OTHER INFORMATION: Probe 3

<400> SEQUENCE: 3
caaacatgag gattacccat gtcgaagaca                              30

<210> SEQ ID NO 4
<211> LENGTH: 21
<212> TYPE: DNA
<213> ORGANISM: Artificial Sequence
<220> FEATURE:
<223> OTHER INFORMATION: Probe 4

<400> SEQUENCE: 4
ccgagaccaa tgtgcgccgt g                                      21

<210> SEQ ID NO 5
<211> LENGTH: 22
<212> TYPE: DNA
<213> ORGANISM: Artificial Sequence
<220> FEATURE:
<223> OTHER INFORMATION: Probe 5

<400> SEQUENCE: 5
aggcgctccg ctaccttgcc ct                                     22

<210> SEQ ID NO 6
<211> LENGTH: 20
<212> TYPE: DNA
<213> ORGANISM: Artificial Sequence
<220> FEATURE:
<223> OTHER INFORMATION: Forward Primer 1

<400> SEQUENCE: 6
tgtggagaga cagggcactg                                        20

<210> SEQ ID NO 7
<211> LENGTH: 25
<212> TYPE: DNA
<213> ORGANISM: Artificial Sequence
<220> FEATURE:
<223> OTHER INFORMATION: Forward Primer 2

<400> SEQUENCE: 7
cgttcacagg cttacaaagt aacct                                  25

<210> SEQ ID NO 8
<211> LENGTH: 19
<212> TYPE: DNA
<213> ORGANISM: Artificial Sequence
<220> FEATURE:
<223> OTHER INFORMATION: Forward Primer 3

<400> SEQUENCE: 8
cctcagcaat cgcagcaaa                                         19

<210> SEQ ID NO 9
<211> LENGTH: 21
<212> TYPE: DNA
<213> ORGANISM: Artificial Sequence
<220> FEATURE:
<223> OTHER INFORMATION: Forward Primer 4

<400> SEQUENCE: 9
gctctgagag cggctctatt g                                      21

-continued

```
<210> SEQ ID NO 10
<211> LENGTH: 17
<212> TYPE: DNA
<213> ORGANISM: Artificial Sequence
<220> FEATURE:
<223> OTHER INFORMATION: Forward Primer 5

<400> SEQUENCE: 10
gtcgcggtaa ttggcgc                                                    17

<210> SEQ ID NO 11
<211> LENGTH: 21
<212> TYPE: DNA
<213> ORGANISM: Artificial Sequence
<220> FEATURE:
<223> OTHER INFORMATION: Reverse Primer 1

<400> SEQUENCE: 11
cagttgttgg ccatacggat t                                               21

<210> SEQ ID NO 12
<211> LENGTH: 20
<212> TYPE: DNA
<213> ORGANISM: Artificial Sequence
<220> FEATURE:
<223> OTHER INFORMATION: Reverse Primer 2

<400> SEQUENCE: 12
ccaacagtct gggttgccac                                                 20

<210> SEQ ID NO 13
<211> LENGTH: 30
<212> TYPE: DNA
<213> ORGANISM: Artificial Sequence
<220> FEATURE:
<223> OTHER INFORMATION: Reverse Primer 3

<400> SEQUENCE: 13
ggaagatcaa tacataaaga gttgaacttc                                      30

<210> SEQ ID NO 14
<211> LENGTH: 18
<212> TYPE: DNA
<213> ORGANISM: Artificial Sequence
<220> FEATURE:
<223> OTHER INFORMATION: Reverse Primer 4

<400> SEQUENCE: 14
cgttatagcg gaccgcgt                                                   18

<210> SEQ ID NO 15
<211> LENGTH: 19
<212> TYPE: DNA
<213> ORGANISM: Artificial Sequence
<220> FEATURE:
<223> OTHER INFORMATION: Reverse Primer 5

<400> SEQUENCE: 15
ggccacgtgt tttgatcga                                                  19

<210> SEQ ID NO 16
<211> LENGTH: 1740
<212> TYPE: DNA
<213> ORGANISM: Enterobacteriophage MS2

<400> SEQUENCE: 16
```

-continued

```
attgcgctcg tgaaggcgta cactgccgct cgtcgcggta attggcgcca ggcgctccgc      60
taccttgccc taaacgaaga tcgaaagttt cgatcaaaac acgtggccgg caggtggttg     120
gagttgcagt tcggttggtt accactaatg agtgatatcc aggtgcata tgagatgctt     180
acgaaggttc accttcaaga gtttcttcct atgagagccg tacgtcaggt cggtactaac    240
atcaagttag atggccgtct gtcgtatcca gctgcaaact tccagacaac gtgcaacata    300
tcgcgacgta tcgtgatatg gttttacata acgatgcac gtttggcatg gttgtcgtct    360
ctaggtatct tgaacccact aggtatagtg tgggaaaagg tgcctttctc attcgttgtc    420
gactggctcc tacctgtagg taacatgctc gagggcctta cggcccccgt gggatgctcc    480
tacatgtcag gaacagttac tgacgtaata acgggtgagt ccatcataag cgttgacgct    540
ccctacgggt ggactgtgga gagacagggc actgctaagg cccaaatctc agccatgcat    600
cgagggtac aatccgtatg ccaacaact ggcgcgtacg taaagtctcc tttctcgatg     660
gtccatacct tagatgcgtt agcattaatc aggcaacggc tctctagata gagccctcaa    720
ccggagtttg aagcatggct tctaacttta ctcagttcgt tctcgtcgac aatggcggaa    780
ctggcgacgt gactgtcgcc ccaagcaact tcgctaacgg ggtcgctgaa tggatcagct    840
ctaactcgcg ttcacaggct tacaaagtaa cctgtagcgt tcgtcagagc tctgcgcaga    900
atcgcaaata caccatcaaa gtcgaggtgc ctaaagtggc aacccagact gttggtggtg    960
tagagcttcc tgtagccgca tggcgttcgt acttaaatat ggaactaacc attccaattt   1020
tcgctacgaa ttccgactgc gagcttattg ttaaggcaat gcaaggtctc ctaaaagatg   1080
gaaacccgat tccctcagca atcgcagcaa actccggcat ctactaatag acgccggcca   1140
ttcaaacatg aggattaccc atgtcgaaga caacaaagaa gttcaactct ttatgtattg   1200
atcttcctcg cgatctttct ctcgaaattt accaatcaat tgcttctgtc gctactggaa   1260
gcggtgatcc gcacagtgac gactttacag caattgctta cttaagggac gaattgctca   1320
caaagcatcc gaccttaggt tctggtaatg acgaggcgac ccgtcgtacc ttagctatcg   1380
ctaagctacg ggaggcgaat ggtgatcgcg gtcagataaa tagagaaggt ttcttacatg   1440
acaaatcctt gtcatgggat ccggatgttt tacaaaccag catccgtagc cttattggca   1500
acctcctctc tggctaccga tcgtcgttgt ttgggcaatg cacgttctcc aacggtgctc   1560
ctatgggca caagttgcag gatgcagcgc cttacaagaa gttcgctgaa caagcaaccg   1620
ttacccccg cgctctgaga gcggctctat tggtccgaga ccaatgtgcg ccgtggatca   1680
gacacgcggt ccgctataac gagtcatatg aatttaggct cgttgtaggg aacggagtgt   1740
```

<210> SEQ ID NO 17
<211> LENGTH: 3569
<212> TYPE: RNA
<213> ORGANISM: Enterobacteriophage MS2

<400> SEQUENCE: 17

```
gggugggacc ccuuucgggg uccugcucaa cuuccugucg agcuaaugcc auuuuuaaug      60
ucuuuagcga gacgcuacca uggcuaucgc uguaggbuagc cggaauucca uuccuaggag    120
guuugaccug ugcgagcuuu uaguacccuu gauagggaga acgagaccuu cgucccucuc    180
guucgcguuu acgcggacgg ugagacugaa gauaacucau ucucuuuaaa auaucguucg    240
aacuggacuc ccggucguuu uaacucgacu ggggccaaaa cgaaacagug gcacuacccc    300
ucuccguauu cacgggggc guuaaguguc acaucgauag aucaaggugc cuacaagcga    360
aguggqucau cguggggucg cccguacgag gagaaagccg guuucggcuu cucccucgac    420
```

```
gcacgcuccu gcuacagccu cuucccugua agccaaaacu ugacuuacau cgaagugccg    480
cagaacguug cgaaccgggc gucgaccgaa guccugcaaa aggucaccca ggguaauuuu    540
aaccuuggug uugcuuuagc agaggccagg ucgacagccu cacaacucgc gacgcaaacc    600
auugcgcucg ugaaggcgua cacugccgcu cgucgcggua auuggcgcca ggcgcuccgc    660
uaccuugccc uaaacgaaga ucgaaaguuu cgaucaaaac acguggccgg caggugguug    720
gaguugcagu ucgguugguu accacuaaug agugauaucc agggugcaua ugagaugcuu    780
acgaagguuc accuucaaga guuucuuccu augagagccg uacgucaggu cgguacuaac    840
aucaaguuag auggccgucu gucguaucca gcugcaaacu ccagacaac gugcaacaua    900 ucgcgacgua ucgugauaug guuuuacaua aacgaugcac guuuggcaug guugucgucu    960
cuagguaucu ugaacccacu agguauagug ugggaaaagg ugccuuucuc auucguuguc   1020
gacuggcucc uaccguuagg uaacaugcuc gagggccuua cggccccccgu gggaugcucc   1080 uacaugucag gaacaguuac ugacguaaua acgggugagu ccaucauaag cguugacgcu   1140
cccuacgggu ggacugugga gagacagggc acugcuaagg cccaaaucuc agccaugcau   1200 cgaggggguac aauccguaug gccaacaacu ggcgcguacg uaaagucucc uuucucgaug   1260
guccauaccu uagaugcguu agcauuaaac aggcaacggc ucucuagaua gagcccucaa   1320
ccggaguuug aagcauggcu ucuaacuuua ucaguucgu ucgcgucgac aauggcggaa    1380
cuggcgacgu gacugucgcc ccaagcaacu ucgcuaacgg ggcgcgaa uggaucagcu    1440 cuaacucgcg uucacaggcu uacaaaguaa ccuuagcgu ucgucagagc ucugcgagaa    1500
aucgcaaaua caccaucaaa gucgaggugc cuaaaguggc aacccagacu guuggugug    1560 uagagcuucc uguagccgca uggcguucgu acuuaaauau ggaacuaacc auuccaauuu   1620
ucgcuacgaa uuccgacugc gagcuuauug uuaaggcaau gcaaggucuc cuaaaagaug   1680
gaaacccgau ucccucagca aucgcagcaa acuccggcau cuacuaauag acgccggcca   1740
uucaaacaug aggauuaccc augucgaaga caacaaagaa guucaacucu uuauguauug   1800
aucuuccucg cgaucuuucu cucgaaauuu accaaucaau ugcuucuguc gcuacuggaa   1860
gcggugaucc gcacagugac gacuuuacag caauugcuua cuuaagggac gaauugcuca   1920
caaagcaucc gaccuuaggu ucugguaaug acgaggcgac ccgucguacc uuagcuaucg   1980
cuaagcuacg ggaggcgaau ggugaucgcg ucagauaaa uagagaaggu ucuuacaug    2040 acaaauccuu gcaugggau ccggauguuu uacaaccag caucccguagc cuuauuggca   2100 accuccucuc uggcuaccga ucgucguugu uugggcaaug cacguucucc aacggugcuc   2160
cuauggggca caaguugcag gaugcagcgc cuuacaagaa guucgcugaa caagcaaccg   2220
uuaccccccg cgcucugaga gcggcucuau uggucgagaa ccaaugugcg ccguggauca   2280
gacacgcggu ccgcuauaac gagucauaug aauuuaggcu cguuguaggg aacgagugu    2340 uuacaguucc gaagaauaau aaaauagauc gggcugccug uaaggagccu gauaugaaua   2400
uguaccucca gaaaggggguc gggugcuuuca ucagacgccg gcucaaaucc guugguauag   2460
accugaauga ucaaucgauc aaccagcguc uggcucagcg gggcagcgua gaugguucgc   2520
uugcgacgau agacuuaucg ucugcaaccg auuccaucuc cgaucgccug gugugaguuu   2580
uucucccacc ugagcuauau ucauaucucg aucguauccg cucacacuac ggaaucuag    2640 auggcgagac gauacgaugg gaacuauuu ccacaaugg aaaugggguc acauuugagc    2700
uagaguccau gauauucugg gcaauaguca aagcgaccca aauccauuuu ggguaacgccg   2760
```

```
                                                          -continued gaaccauagg caucuacggg gacgauauua uaugucccag ugagauugca ccccgugugc    2820
uagaggcacu ugccuacuac gguuuuaaac cgaaucuucg uaaaacguuc guguccgggc    2880
ucuuucgcga gagcugcggc gcgcacuuuu accguggugu cgaugucaaa ccguuuuaca    2940
ucaagaaacc uguugacaau cucuucgccc ugaugcugau auuaaaucgg cuacggguu     3000 ggggaguugu cggagguaug ucagauccac gccucuauaa ggugugggua cggcucuccu    3060
cccaggugcc uucgauguuc uucgguggga cggaccucgc ugccgacuac uacguaguca    3120
gcccgccuac ggcagucucg guauacacca agacuccgua cgggcggcug cucgcggaua    3180
cccguaccuc ggguuuccgu cuugcucgua ucgcucgaga acgcaaguuc uucagcgaaa    3240
agcacgacag uggucgcuac auagcguggu uccauacugg aggugaaauc accgacagca    3300
ugaaguccgc cggcgugcgc guuauacgca cuucggagug gcuaacgccg guucccacau    3360
ucccucagga guguggcca gcgagcucuc cucgguagcu gaccgaggga ccccguaaa      3420 cggggugggu gugcucgaaa gagcacggu gcgaaagcgg uccggcucca ccgaaaggug    3480
ggcgggcuuc ggcccaggga ccuccccua aagagaggac ccgggauucu cccgauuugg    3540
uaacuagcug cuuggcuagu uaccaccca                                      3569
```

METHODS FOR DETECTING BACTERIOPHAGE MS2

RELATED APPLICATION

This Application claims the benefit of priority from U.S. Provisional Application Ser. No. 60/383,999, filed on May 29, 2002.

This application is a division of application Ser. No. 10/328,226 filed Dec. 23, 2002, now U.S. Pat. No. 6,841,346.

GOVERNMENTAL INTEREST

The invention described herein may be manufactured, used and licensed by or for the U.S. Government.

FIELD OF THE INVENTION

The present invention is related generally to the detection of biological agents, and more particularly to assays comprising nucleic acid probes and primers, and methods of using the same for detecting nucleic acids from bacteriophage MS2 in a sample.

BACKGROUND OF THE INVENTION

Proliferation of biological weapons throughout the world has made accurate monitoring and detection of pathogenic biological agents ever more critical. Many of the biological detection systems currently in service and under development routinely require testing and retesting to ensure proper operation under field and laboratory conditions. Appreciating the risks of handling actual biological agents, non-pathogenic agents that possess similar detection characteristics or features are preferably used as a safer alternative for testing such systems.

One non-pathogenic biological agent, Enterobacteriophage MS2, referred herein as "bacteriophage MS2", has been found to be well suited for simulating pathogenic biological agents particularly viral pathogens that are extremely harmful to humans and animals. Bacteriophage MS2 is a very small virus having a genome composed of ribonucleic acid (RNA). Current bacteriophage MS2 test assays typically experience low sensitivity and precision, and slow data acquisition and analysis. Moreover, the current test assays have poor specificity to the bacteriophage producing frequent false positives and high background noise. Test assays currently used are also complicated and require extensive sample processing, resulting in increased labor and costs.

Accordingly, there is a need for an assay and a method of detecting bacteriophage MS2 that is rapid, accurate and cost effective to implement. It would be also desirable to provide novel nucleic acid probes and primers useful for providing rapid and specific detection of bacteriophage MS2 in samples. There is a further need to develop assays for the detection of the non-pathogenic agent bacteriophage MS2 as a reliable prognosticator of the presence of pathogens having a sufficiently similar genetic profile.

SUMMARY OF THE INVENTION

The present invention relates to the detection of bacteriophage MS2 in samples as a reliable prognosticator for the detection of pathogenic species.

In one aspect of the present invention there is provided a method of detecting bacteriophage MS2, comprising contacting nucleic acid present in a sample suspected of emanating from the MS2 bacteriophage, the nucleic acid including a target nucleic acid sequence particularly associated with MS2 bacteriophage with a nucleic acid probe capable of selectively hybridizing to at least a portion of the target nucleic acid sequence. In a preferred embodiment, the method further comprises detecting the presence of the bacteriophage MS2 as a consequence of the selective hybridization of the nucleic acid probe to the target nucleic acid sequence.

In another aspect of the present invention, there is provided a nucleic acid in the form of a nucleic acid probe for detecting bacteriophage MS2, comprising a nucleic acid sequence selected from [SEQ ID NO:1], [SEQ ID NO:2], [SEQ ID NO:3], [SEQ ID NO:4] and [SEQ ID NO:5].

In another aspect of the present invention, there is provided a nucleic acid in the form of a forward primer for amplifying a target nucleic acid particularly associated with MS2 bacteriophage, comprising a nucleic acid sequence selected from the group consisting of [SEQ ID NO:6], [SEQ ID NO:7], [SEQ ID NO:8], [SEQ ID NO:9] and [SEQ ID NO:10].

In another aspect of the present invention, there is provided a nucleic acid in the form of a reverse primer for amplifying a target nucleic acid particularly associated with MS2 bacteriophage, comprising a nucleic acid sequence selected from the group consisting of [SEQ ID NO:11], [SEQ ID NO:12], [SEQ ID NO:13], [SEQ ID NO:14] and [SEQ ID NO:15]. Each of the reverse primers listed herein operatively correspond to one of the forward primers described above.

The invention also includes a kit for detecting a target nucleic acid sequence particularly associated with bacteriophage MS2, the kit comprising a nucleic acid probe component having a nucleic acid sequence selected from the group consisting of [SEQ ID NO:1], [SEQ ID NO:2], [SEQ ID NO:3], [SEQ ID NO:4], [SEQ ID NO:5] and combinations thereof, a nucleic acid forward primer component having a nucleic acid sequence selected from the group consisting of [SEQ ID NO:6], [SEQ ID NO:7], [SEQ ID NO:8], [SEQ ID NO:9], [SEQ ID NO:10] and combinations thereof, and a nucleic acid reverse primer component each corresponding to a corresponding forward primer and having a nucleic acid sequence selected from the group consisting of [SEQ ID NO:11], [SEQ ID NO:12], [SEQ ID NO:13], [SEQ ID NO:14], [SEQ ID NO:15] and combinations thereof.

BRIEF DESCRIPTION OF THE DRAWINGS

The following drawings are illustrative of embodiments of the present invention and are not intended to limit the invention as encompassed by the claims forming part of the application.

FIGS. 1A, 1B and 1C depict a target gene region [SEQ ID NO:16] of a bacteriophage MS2 genome [SEQ ID NO:17] wherein sequences indicated by a single line represent preferred forward primers [SEQ ID NO:6 through 10], respectively, wherein sequences indicated by double lines represent nucleic acid complements of preferred reverse primers [SEQ ID NO:11 through 15], respectively, and wherein sequences indicated by dotted lines represent preferred nucleic acid probes [SEQ ID NO:1 through 5], respectively, in accordance with the present invention.

DETAILED DESCRIPTION OF THE INVENTION

The present invention relates generally to assays and methods of detecting bacteriophage MS2 in a sample. The present invention provides rapid detection of bacteriophage that is less prone to error, reduces false positives and background noise through substantial reductions in nonspecific amplification or hybridization of a target nucleic acid sequence particularly associated with bacteriophage MS2, thereby revealing a more accurate signal and detection thereof. The present invention is further directed to isolated nucleic acids in the form of primers including forward and reverse primers and in the form of nucleic acid probes, which have been found to be useful for implementing specific detection of bacteriophage MS2 in samples. Each of the isolated nucleic acids of the present invention comprise a nucleic acid sequence that is complementary to a portion of the nucleic acid derived specifically from bacteriophage MS2. The method of the present invention provides sensitive and precise detection of bacteriophage MS2 that can be implemented in a rapid and cost effective manner.

The term "sample" as used herein means to encompass any sample suspected of containing the intended target nucleic acid, and includes, but is not limited to, biological samples, body fluids, environmental samples, food samples, and laboratory samples and combinations thereof.

The term "oligonucleotide" as used herein means a single-stranded nucleotide polymer of greater than 2 nucleotides in length, preferably from about 10 to 100 nucleotides, most preferably from about 12 to 50 nucleotides in length. Such oligonucleotides may be joined by phosphodiester linkages, by phosphorothioate linkages, or by other rare or non-naturally-occurring linkages. Furthermore, an oligonucleotide may have uncommon nucleotides or non-nucleotide moieties. An oligonucleotide as defined herein is a nucleic acid, preferably DNA, but may be RNA or have a combination of ribo- and deoxyribonucleotides covalently linked. Nucleic acid probes and primers of a defined sequence may be produced by techniques known to those of ordinary skill in the art, such as by chemical or biochemical synthesis, and by in vitro or in vivo expression from recombinant nucleic acid molecules, e.g., bacterial or retroviral vectors.

The terms "target nucleic acid sequence", "target nucleotide sequence" or "target sequence" are meant a specific desired deoxyribonucleotide or ribonucleotide sequence comprising all or a part of the nucleotide sequence of a single-stranded target nucleic acid molecule, and the deoxyribonucleotide or ribonucleotide sequence perfectly complementary thereto.

"Stringent" hybridization assay conditions refer to conditions wherein a specific nucleic acid probe is able to hybridize with target nucleic acids (preferably RNA of bacteriophage MS2) and not to an adverse extent with other nucleic acids present in the sample derived either from other organisms or other sources. It will be appreciated that these conditions may vary depending upon factors including the guanine-cytosine content and length of the probe, the hybridization temperature, the composition of the hybridization reagent or solution, and the degree of hybridization specificity sought. Examples of specific stringent hybridization conditions are provided in the disclosure below.

The term "probe" as used herein means a single-stranded oligonucleotide having a sequence partly or completely complementary to a nucleic acid sequence sought to be detected, so as to stably hybridize thereto under stringent hybridization conditions. In the case of a group or species-specific probe, the probe has the ability to stably hybridize to a target nucleic acid and not to non-target nucleic acids such as those from organisms outside the phylogenetic group or species of interest under stringent hybridization conditions. Probes may, but need not, have regions which are not complementary to a target sequence, as long as such sequences do not substantially alter the probe's desired specificity under stringent hybridization conditions. The probe may be labeled with a reporter group or label moiety such as, for example, a radioisotope, a fluorescent or chemiluminescent moiety, with an enzyme or other ligand, which can be used for detection or confirmation that the probe has hybridized to the target sequence.

The present invention is directed to a nucleic acid probe having a nucleic acid sequence selected from a group of specific sequences and that the probe, as a basic and novel characteristic, will form a stable hybrid with a nucleic acid in a nucleotide sequence region having a nucleotide sequence complementary to one of the listed nucleic acid sequences of the group under stringent hybridization conditions. The present invention also encompasses the complement of the corresponding DNA or RNA sequence listed herein.

The term "primer" as used herein means an oligonucleotide capable of hybridizing to a region corresponding to a target nucleic acid sequence thereby acting as a starting site or location for initiating nucleic acid amplification, and the term encompasses both the forward and reverse primers. A primer as defined herein will preferably be from about 10 to 100 nucleotides in length; more preferably from about 10 to 50 nucleotides in length The term "primer extending reagent" as used herein encompasses any biologically active reagent or macromolecule that is capable of initiating the formation and repair of nucleic acid including extension of polymers or nucleic acids, typically associated with nucleic acid amplification. Typical examples of such reagents include DNA polymerases such as *E. coli* DNA polymerase 1, thermostable DNA polymerase from *Thermus aquaticus* (Taq), and thermostable DNA polymerase from *Bacillus stearothermophilus* (Bst).

The term "nucleic acid hybrid" or "hybrid" as used herein means a nucleic acid structure containing a double-stranded, hydrogen-bonded region, preferably from about 10 to 100 nucleotides in length, and most preferably from about 12 to 50 nucleotides in length, wherein each strand is complementary to the other and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

The term "complementary" as used herein means that the nucleotide sequences of similar regions of two single-stranded nucleic acids, or different regions of the same single-stranded nucleic acid have a nucleotide base composition that allows the single strands to hybridize together in a stable double-stranded hydrogen-bonded region under stringent hybridization conditions. When a contiguous sequence of nucleotides of one single stranded region is able to form a series of hydrogen-bonded base pairs with an analogous sequence of nucleotides of the other single-stranded region such that A is paired with U or T, and C is paired with G, the nucleotides sequences are complementary.

The term "nucleic acid amplification" or "target amplification" as used herein means increasing the number of identical nucleic acid molecules through replication of the desired specific segment or portion of the nucleic acid.

In one aspect of the present invention, there is provided a nucleic acid probe having a specific nucleic acid sequence complementary to at least a portion of a target nucleic acid sequence specific to the bacteriophage MS2. In a preferred embodiment of the present invention, the probe comprises a nucleic acid sequence that may be selected from [SEQ ID NO: 1] through [SEQ ID NO: 5].

In another aspect of the present invention, there is provided a primer having a nucleic acid sequence complementary to a portion of a nucleic acid sequence corresponding to a target nucleic acid specific to the bacteriophage MS2. In a preferred embodiment of the present invention, the primers typically present in the form of primer pairs including forward primers and reverse primers where the forward primers include a nucleic acid sequence that may be selected from [SEQ ID NO:6] through [SEQ ID NO: 10], and where the corresponding reverse primers may be selected from [SEQ ID NO: 11] through [SEQ ID NO: 15].

In a general aspect of the present invention, the forward and reverse primers and nucleic acid probes are designed to be complementary to specific nucleic acid regions of bacteriophage MS2 RNA or the DNA encoding it, or to an oligonucleotide or nucleic acid comprising a target nucleic acid sequence specific to bacteriophage MS2.

The probes of the present invention are designed to hybridize specifically to a portion of a target nucleic acid sequence specifically derived from bacteriophage MS2 under conditions, which would allow the specific detection of the target nucleic acid sequence.

The primers of the present invention are designed and/or selected to hybridize to a nucleic acid sequence, which lies to the 3' side of a target nucleic acid sequence of the target genome. The hybridized primer prepares the site for nucleic acid amplification to generate a nucleic acid strand complementary to at least a portion of the target nucleic acid sequence. The newly formed strand also contains the target nucleic acid sequence.

Accordingly, a basic and novel characteristic of the probes and the primers of the present invention is their ability, under appropriate hybridization reaction conditions, to preferentially hybridize to a predetermined region of a target nucleic acid specifically derived from bacteriophage MS2 over non-targeted nucleic acids or nucleic acid regions. This specificity is related to the extent of the match between the target nucleic acid sequences and primer or probe involved in the formation of the hybridization complex, and the hybridization reaction conditions.

The present invention further describes double stranded nucleic acid hybrid molecules formed between the probes or primers and their specific target nucleic acid sequences. Hybrids formed between labeled probes and target nucleic acid sequences are useful for the qualitative and/or quantitative detection of bacteriophage MS2. These structures may be physically or chemically distinguishable from unhybridized labeled probes after the hybridization reaction based on the label and detection system employed.

Similarly, the hybrids of the present invention formed between the primers and their complementary nucleic acid regions associated with the target nucleic acid sequence provide an initiation site for at least one cycle of nucleic acid synthesis or replication, reverse transcription and the like. The resulting amplified nucleic acid may then be detected using a probe to form a detectable hybrid molecule. In another embodiment of the present invention, the actual formation of the hybrid molecule produces a detectable event as will be further described hereinafter.

Nucleic acid hybridization is the process by which two nucleic acid strands having completely or partially complementary nucleotide sequences come together under predetermined reaction conditions to form a stable, double-stranded hybrid with specific hydrogen bonds. Either nucleic acid strand may be a deoxyribonucleic acid (DNA) or a ribonucleic acid (RNA); thus hybridization can involve RNA:RNA hybrids, DNA:DNA hybrids, or RNA:DNA hybrids.

Thus, as used in this application, the term "hybridization" refers to the ability of two completely or partly complementary single nucleic acid strands to come together to form a stable structure having a double-stranded region. The two constituent strands of this double-stranded structure, sometimes called a hybrid, are held together with hydrogen bonds. Although these hydrogen bonds most commonly form between nucleotides containing the bases adenine and thymine or uracil (A and T or U) or cytosine and guanine (C and G), base pairing can form between other combinations of bases, who are not members of these "canonical" pairs. Non-canonical base pairing is well-known in the art.

Nucleic acid hybridization is a common method for detecting and quantifying target nucleic acids having one or more specific nucleotide sequences. Such methods are useful for identifying and classifying organisms, diagnosing infectious diseases and genetic abnormalities, testing food and drugs, and identifying criminal suspects, among numerous other things. Typically, nucleic acid hybridization assays use a labeled oligonucleotide hybridization assay probe having a nucleic acid sequence complementary to the target sequence. Such labels are well known in the art, and may include radioactive isotopes, enzymes, or fluorescent, luminescent, or chemiluminescent groups. The probe is mixed with a sample suspected of containing a nucleic acid having the target nucleic acid sequence under hybridization conditions suitable for allowing annealing of the two strands by hydrogen bonding in the region of complementarity. The probe then hybridizes to the target nucleic acid present in the sample. The resulting hybrid duplex may be detected by any suitable technique known in the art.

The term "homologous" refers to the subunit sequence similarity between two polymeric molecules including nucleic acid molecules, DNA or RNA molecules, or polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

A first oligonucleotide anneals with a second oligonucleotide with high stringency if the two oligonucleotides anneal under conditions whereby only oligonucleotides which are at least about 70%, and preferably at least about 90% or, more preferably, at least about 95%, complementary anneal with one another. The stringency of conditions used to anneal two oligonucleotides is a function of, for example, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

Often a sample will not contain a sufficient quantity of nucleic acid molecules to permit direct detection by nucleic acid hybridization due to the sensitivity limits of the particular label used. In such a case, the amount of detectable target nucleotide sequence is increased before nucleic acid hybridization is used for detection. This procedure is termed nucleic acid amplification, and the method of increasing the amount of the target nucleic acid is referred to as amplifying the target nucleic acid or target nucleotide sequence.

A polymerase chain reaction (PCR) assay using genomic bacteriophage MS2 RNA [SEQ ID NO:17] encoding specific regions or target nucleic acid sequences which form at least a portion of a target nucleic acid region [SEQ ID NO:16], may preferably be used in practicing the present invention for detecting bacteriophage MS2 RNA in a sample. However, the invention should not be construed as being limited to using RNA as a starting point for replication or even to being limited to the particular portion of the bacteriophage MS2 disclosed. Regardless of the starting point, it is preferred that the target nucleic acid sequence being amplified is unique to bacteriophage MS2 to the extent that cross-hybridization and/or amplification of other nucleic acids does not appreciably occur. Preferably the target nucleic acid sequence is not present in other related species or in other pathogens. By using a sufficiently unique target nucleic acid sequence, any amplification product produced during the amplification step will not be complementary to and therefore, will not cross-hybridize and/or amplify the nucleic acids of other organisms under high stringency conditions.

Amplification methods involve the use of at least one nucleic acid strand containing a target nucleotide sequence as a template in a nucleic acid polymerizing reaction to produce a complementary second strand containing the target nucleotide sequence. By repeating this process, using the product nucleic acids as templates in subsequent cycles, the number of nucleic acid molecules having the target nucleotide sequence increases rapidly.

Polymerase chain reaction (PCR) methods are the preferred amplification methods used in the amplification step of the present invention. See e.g., Mullis et al., U.S. Pat. No. 4,683,195, the content of which is incorporated herein by reference. However, the amplification step may also be carried out using any suitable amplification technique known in the art or to be developed.

In the preferred PCR amplification procedure used in the present method, a target nucleic acid unique to the bacteriophage MS2 is amplified by treating the double-stranded nucleic acid with two nucleic acid primers, each being at least complementary to one of the two strands of the target. The primers hybridize with their complementary strands and extension products are synthesized using DNA polymerase and at least four deoxyribonucleotide triphosphates (dNTPs). The extension products are separated from their complementary strands by denaturation at an elevated temperature, typically ranging from about 80° C. to 100° C. The reaction mixture is repeatedly cycled between a low temperature annealing step usually ranging from about 37° C. to 70° C. during which the primers hybridize to their complementary strands, an intermediate temperature (from about 70° C. to 80° C.) primer extension step, to the higher temperature denaturation step at a temperature of from about 80° C. to 100° C. These temperature steps, collectively referred to as "thermal cycling", are repeated many times, typically about 20 to about 40 cycles are carried out, followed by a final synthesis step at about 70° C. and a 4° C. soak to stop the reaction.

PCR reagents, apart from the target nucleic acid sequence, are needed to perform the PCR process. These PCR reagents generally include five classes of components: (i) an aqueous buffer, (ii) a water soluble magnesium salt, (iii) at least four deoxyribonucleotide triphosphates (dNTPs) (conventionally, dATP, dTTP, dGTP, dCTP), (iv) oligonucleotide primers (typically two primers for each target sequence, the sequences defining the 5' ends of the two complementary strands of the double-stranded target sequence), and (v) a polynucleotide polymerase, preferably a DNA polymerase, more preferably a thermostable DNA polymerase, ie., a DNA polymerase which can tolerate temperatures between 90° C. and 100° C. for a total time of at least 10 minutes without losing more than about half its activity.

Primers for the amplification steps are the same if used for a reverse transcription step at the outset to convert RNA into DNA before carrying out the amplification procedure. Preferably, primers are chosen which only amplify target nucleic acid sequences unique to bacteriophage MS2. In the present invention, the primers amplify only a corresponding target nucleic acid sequence within bacteriophage MS2.

Preferred primer pairs and probes target a region of the gene sequence of bacteriophage MS2 are shown in FIGS. 1A, 1B and 1C. Preferred primer pairs include [SEQ ID NO:6] and [SEQ ID NO:11]; [SEQ ID NO:7] and [SEQ ID NO:12]; [SEQ ID NO:8] and [SEQ ID NO:13]; and [SEQ ID NO:9] and [SEQ ID NO:14] are used for standard PCR. Each primer set has an internal nucleic acid probe including [SEQ ID NO:1], [SEQ ID NO:2], [SEQ ID NO:3], [SEQ ID NO:4] and [SEQ ID NO:5], which can be used to confirm the identity of the amplification product by PCR amplification.

It will be understood by those skilled in the art that other target RNA sequences specific for bacteriophage MS2 other than the target region [SEQ ID NO: 16] of the gene RNA shown in FIGS. 1A, 1B and 1C, respectively, may be used to specifically identify bacteriophage MS2 in a sample using PCR-based methods, and other similar methods. However, in the present invention, the target nucleic acid sequence and the portion of the amplified target sequence to which the PCR nucleic acid probe hybridizes are sufficiently unique to bacteriophage MS2 that the probe and primers do not materially hybridize to nucleic acids of other organisms under conditions of high stringency. Thus, the nucleic acid-based detection method of the present invention only detects amplification of the specific, unique bacteriophage MS2 target nucleic acid sequence and not that of other organisms which may be present in the sample.

In the standard PCR assay, the amplified target nucleic acid sequence can be detected directly by any method that can distinguish among the different lengths of DNA. Electrophoresis through agarose gels is the standard method known in the art for use in separating, identifying, and purifying DNA fragments following PCR. The location of the DNA within the gel can be determined directly by staining the gel with low concentrations of an intercalating fluorescent dye, for example, ethidium bromide (EtBr). Band(s) corresponding to the predicted length for the amplified target DNA can then be detected by direct examination of the gel in ultraviolet light.

Additionally, the DNA bands from an electrophoresed sample can be probed by Southern blotting using a single-stranded nucleic acid probe which is complementary to a sequence located between the two selected nucleic acid primers in the amplified target nucleic acid sequence. Usually, the nucleic acid probe is labeled with a radioactive or fluorescent tag, or attached directly or indirectly to an enzyme molecule such that the probe specifically bound to the immobilized complementary target nucleic acid sequence may be localized.

In the preferred embodiment herein, the nucleic acid probe is complementary to at least a portion of the target region [SEQ ID NO:16] of bacteriophage MS2 shown in FIGS. 1A, 1B and 1C. However, the present invention is not limited to this sequence or to this gene region. Rather, the nucleic acid probe may be selected to hybridize to any amplified target nucleic acid sequence located between two primer pairs all of which hybridize to a sequence in bacteriophage MS2 but which do not materially hybridize to the nucleic acid of any other organism that may be present in the sample of interest so as to adversely affect the qualitative and/or quantitative detection of the target region of bacteriophage MS2.

The nucleic acids or oligonucleotides used in the invention may be synthesized by any standard known method or one to be developed.

The nucleic acid probes of the present invention are preferably conveniently synthesized on an automated DNA synthesizer such as a Perkin-Elmer Model 392 or 394 DNA/RNA synthesizer available from Perkin-Elmer Inc. of Foster City, Calif. using standard chemical methods, such as, for example, phosphoramidite chemistry as known in the art. Alternative chemical methods resulting in non-natural backbone groups, such as phosphorothioate, phosphoramidate, and the like, may also be used provided the hybridization efficiencies of the resulting nucleic acids or oligonucleotides are not adversely affected.

Preferably, the nucleic acid probe is composed of from about 15 to 150 nucleotides in length. The precise sequence and length of a nucleic acid probe of the present invention depends in part on the nature of the target nucleic acid sequence to which it hybridizes. The binding location and length may be varied to achieve appropriate annealing and melting properties for a particular embodiment by one skilled in the art in accordance with known techniques such as "Taqman"-type assays.

Nucleic acids or oligonucleotides of the present invention include linear oligomers of natural or modified monomers or linkages, such as deoxyribonucleotides, ribonucleotides, and the like, which are capable of specifically binding to a target nucleic acid by way of a regular pattern of monomer-to-monomer interactions, such as Watson-Crick base pairing. Usually, monomers are linked by phosphodiester bonds or their analogs to form oligonucleotides ranging in size from a few monomeric units, e.g., 3 to 4, to several tens of monomeric units. Whenever an oligonucleotide is represented by a sequence of letters, such as "ATGCCTG," it will be understood that the nucleotides are in a 5' to 3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphoranilidate, phosphoramidate, and similar compounds.

In another important aspect of the nucleic acid probes of the present invention, the probes may further include a reporter and a quencher, each attached to the oligonucleotide. During PCR, the modified probe is designed to generate a detectable signal to indicate that it has hybridized with the target nucleic acid sequence. The reporter is a molecule typically in the form of a dye which can generate a detectable signal (e.g., fluorescence), and the quencher is a molecule which when placed in close proximity to the reporter is capable of substantially reducing or quenching the intensity of the detectable signal.

As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

As used herein, the terms "quenching" and "fluorescence energy transfer" refer to the process whereby when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, it has been assumed that the reporter and the quencher be preferably attached to the probe within a few nucleotides of one another, usually with a separation of from about 6 to 16 nucleotides. Typically, this separation is achieved by attaching one member of a reporter-quencher pair to the 5' end of the probe and the other member to a nucleotide about 6 to 16 nucleotides away.

Preferably, the reporter may be selected from fluorescent organic dyes modified with a suitable linking group for attachment to the terminal 3' carbon or terminal 5' carbon of the probe. The quencher may also be selected from organic dyes, which may or may not be fluorescent, depending on the embodiment of the present invention. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, In: Handbook of Fluorescence Spectra of Aromatic Molecules, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, In: Handbook of Fluorescent Probes and Research Chemicals, Molecular Probes of Eugene, Oreg., 1992, the content of which is incorporated herein by reference.

Preferred reporter-quencher pairs may be selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another preferred group of fluorescent compounds for use as reporters are the naphthylamines, having an amino group in the alpha or beta position. Included among such naphthylamino compounds are 1-demethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl) phenyl)maleimide; benzoxadiazoles; stilbenes; pyrenes and the like.

Most preferably, the reporters and quenchers are selected from fluorescein and rhodamine dyes. These dyes and appropriate linking methodologies for attachment to oligonucleotides are well known in the art.

Suitable examples of quenchers may selected from 6-carboxy-tetramethyl-rhodamine, 4-(4-dimethylaminophenylazo) benzoic acid (DABYL), tetramethylrhodamine (TAMRA), BHQ-0™, BHQ-2™, and BHQ-3™, each of which are available from Bioresearch Technologies, Inc. of Novato in California, QSY-7™, QSY-9™, QSY-21™ and QSY-35™, each of which are available from Molecular Probes, Inc., and the like.

Suitable examples of reporters may selected from dyes such as SYBR green, 5-carboxyfluorescein (5-FAM™ available from Applied Biosystems of Foster City in California), tetrachloro-6-carboxyfluorescein, 2,7-dimethoxy-4,5-dichloro-6-carboxyfluorescein, hexachloro-6-carboxyfluorescein, 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like.

In one embodiment of the present invention, the probe may be attached at the 5' end with a reporter selected from fluorescein such as 6-carboxyfluorescein (6-FAM) and a quencher selected from rhodamine such as 6-carboxy-tetramethyl-rhodamine (TAMRA) which may be attached to any T position or at the 3' end thereof as described in Livak et al., Guidelines for Designing TaqMan™ Fluorogenic Probes for 5' Nuclease Assays, In: Perkin Elmer Research News, 1995, Applied Biosystems Division of Foster City in California, the content of which is incorporated herein by reference. Preferably, the probe may be adapted to have a higher melt temperature ($T_m$) than the primers, and during the extension phase, the probe is at least substantially hybridized to the target nucleic acid sequence.

It will be understood based on this disclosure that the invention is not limited to this particular reporter-quencher pair or to the particular linkages used to attach the molecules to the probe. Rather, as previously discussed herein, a wide variety of reporter-quencher pairs may be attached to the oligonucleotide probe by a variety of linkages. Further, the reporter-quencher pair need not be located on nucleotides which are immediately adjacent, instead, the quencher may be attached to any nucleotide on the probe and still quench the fluorescence emission of the reporter attached to the 5' end thereof.

In another preferred embodiment, amplification of the target nucleic acid sequence may be detected by measuring the fluorescence of the reaction mixture in the presence of a thermostable intercalating fluorescent dye such as ethidium bromide (EtBr), or SYBR green 1 available from Qualicon of Wilmington in Delaware. The fluorescence detects the formation of any double-stranded DNA and is an indication that the target sequence specified by the primer pair has been produced.

There are many linking moieties and methodologies for attaching reporters and quenchers to the 5' or 3' termini of oligonucleotides well known in the art. Preferably, commercially available linking moieties are employed that can be attached to an oligonucleotide during synthesis. Suitable moieties are available from Clontech Laboratories of Palo Alto in California.

Rhodamine and fluorescein dyes may be conveniently attached to the 5' hydroxyl of an oligonucleotide at the conclusion of solid phase synthesis by way of dyes derivatized with a phosphoramidite moiety as known in the art.

It will be understood that the invention is not limited to the release of a reporter from the nucleic acid probe in order to cause fluorescence of a sample as the target DNA is amplified. Rather, one skilled in the art would recognize that other techniques for detecting amplification as known in the art may also be used. For example, techniques such as PCR-based quantitative sequence detection (QSD) may be performed using nucleic acid probes which, when present in the single-stranded state in solution, are configured such that the reporter and quencher are sufficiently close to substantially quench the reporter's emission. However, upon hybridization of the intact reporter-quencher, nucleic acid probe with the amplified target nucleic acid sequence, the reporter and quenchers become sufficiently distant from each other. As a result, the quenching is substantially abated causing an increase in the fluorescence emission detected.

The method of the present invention may include differential quenching of the reporter due to the interaction of the reporter-quencher probe with the amplified target nucleic acid sequence. The precise mechanism by which the reporter-quenchers are brought together or taken apart may vary. Guidelines for designing, producing, and using appropriate reporter-quencher nucleic acid probes are known in the art and are described in the above-cited references including, for example, Livak et al., Guidelines for Designing TaqMan™ Fluorogenic Probes for 5' Nuclease Assays, In: Perkin Elmer Research News, 1995, Applied Biosystems Division of Foster City, Calif., the content of which are incorporated herein by reference.

The 3' terminal nucleotide of the nucleic acid probe may be rendered incapable of extension by a nucleic acid polymerase in one embodiment of the invention. Such blocking may be carried out by the attachment of a reporter or quencher to the terminal 3' carbon of the nucleic acid probe by a linking moiety, or by making the 3'-terminal nucleotide a dideoxynucleotide. Alternatively, the 3' end of the nucleic acid probe may be rendered impervious to the 3' to 5' extension activity of a polymerase by incorporating one or more modified internucleotide linkages onto the 3' end of the oligonucleotide. Minimally, the 3' terminal internucleotide linkage must be modified, however, additional internucleotide linkages may be modified. It is preferred that the 5' to 3' exonuclease ability of the DNA polymerase to cleave off the 5' nucleotide to which the reporter is attached remains preserved.

Internucleotide modifications which prevent elongation from the 3' end of the nucleic acid probe and/or which block the 3' to 5' exonuclease activity of the DNA polymerase during PCR may include phosphorothioate linkages, methylphosphonate linkages, boranophosphate linkages, and other similar polymerase-resistant internucleotide linkages. An alternative method to block 3' extension of the probe is to form an adduct at the 3' end of the probe using mitomycin C or other like antitumor antibiotics such as described in Basu et al., Biochemistry 32:4708-4718, 1993. Thus, the precise mechanism by which the 3' end of the nucleic acid probe is protected from cleavage is not essential so long as the quencher is not cleaved from the nucleic acid probe.

The level of fluorescence is preferably measured using a laser/fluorometer such as, for example, an ABI Prism Model 7700 or 7900 Sequence Detector or a BAX™ fluorometer. However, similar detection systems for measuring the level of fluorescence in a sample are included in the invention.

In a preferred embodiment, amplification of the bacteriophage MS2-specific target sequence specified by the primer pair is detected by QSD. Preferably, a Model 7700 or 7900 Sequence Detector laser fluorometer/thermal cycler is used for the QSD procedure to detect the fluorescence of the PCR sample mixture before and after each round of amplification. Such a QSD procedure is described in Heid et al., Genome Res. 6:986-994, 1996, the content of which is incorporated herein by reference.

QSD is similar to standard PCR assays in that DNA is used as a DNA template to generate millions of copies of the target DNA by *Thermus aquaticus* (Taq) DNA polymerase enzyme and thermal cycling. However, QSD differs significantly from PCR in that QSD involves the detection of the hybridization of a nonextendible internal fluorogenic reporter-quencher DNA probe (e.g., a TaqMan™ probe available from Perkin Elmer) which contains a reporter at one end and a quencher on the other end and which is specific for the target DNA sequence being amplified as described in Heid et al., Genome Res. 6:986-994, 1996. When the probe is intact, fluorescent energy transfer occurs and the reporter dye fluorescence is absorbed by the quenching dye. During the extension phase of the PCR cycle, the fluorescent hybridization probe is cleaved by the 5' to 3' exonuclease activity of the DNA polymerase. Once the probe is cleaved, the reporter dye emission is no longer quenched resulting in an increase of the reporter dye fluorescence emission spectra after each round of replication.

The present invention also includes a kit for detecting bacteriophage MS2 nucleic acid. The kit comprises at least one primer pair, each of which is capable of amplifying a unique target sequence of the bacteriophage MS2 genome. In a preferred embodiment, the target bacteriophage MS2 nucleic acid is the gene region [SEQ ID NO:16], and the forward and reverse primer pairs having the sequences selected from [SEQ ID NO:5] and [SEQ ID NO:9]; [SEQ ID NO:6] and [SEQ ID NO:10]; [SEQ ID NO:7] and [SEQ ID NO:11]; and [SEQ ID NO:8] and [SEQ ID NO:12], respectively. In another preferred embodiment, the nucleic acid probe used to detect the amplification product has a sequence selected from [SEQ ID NO:1 through 5]. However, the present invention is not limited to these primers or nucleic acid probe sequences. Rather, any nucleic acid probe having a sequence between the two primers spanning from nucleotide residue 601 up to and including nucleotide residue 2340 of the genome of bacteriophage MS2 [SEQ ID NO:17] is encompassed in the present invention.

The kit is used pursuant to the methods disclosed in the invention. Further, the kit may be used in standard PCR, or in a homogeneous format PCR procedure as known in the art. One skilled in the art would appreciate based on the disclosure herein that the kit may used in any of the aforementioned procedures and in any combination thereof.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

---

What is claimed is:

1. A method of detecting bacteriophage MS2 in a sample, comprising:

(a) contacting the sample with polymerase chain reaction reagents specific for a bacteriophage MS2 target nucleic acid sequence, said polymerase chain reaction reagents including a pair of forward and reverse primers having nucleotide sequences of SEQ ID NO: 7 as forward primer, and SEQ ID NO: 12 as reverse primer; a polymerase enzyme; and a nucleic acid probe, wherein said probe is SEQ ID NO: 2 and further comprises:
  a reporter attached to the 5' end of the nucleic acid probe, said reporter capable of emitting a detectable signal; and
  a quencher attached to the 3' end of the nucleic acid probe, which is capable of substantially quenching the reporter and preventing the emission of the detectable signal when the nucleic acid probe is intact, wherein the reporter becomes substantially unquenched when the nucleic acid probe is cleaved by the polymerase enzyme during amplification of the target nucleic acid sequence of the bacteriophage MS2;

(b) amplifying said target nucleic acid sequence by thermal cycling, wherein the thermal cycling is sufficient to amplify the target acid sequence; and (c) measuring the level of detectable signal, which correlates to an amount of bacteriophage MS2 present in the sample, thereby quantitatively detecting a bacteriophage MS2 in the sample;

and wherein said detection method only detects the presence of bacteriophage MS2 and not other organisms which may be present in the sample.

* * * * *